United States Patent
Alkan et al.

(10) Patent No.: US 12,056,584 B2
(45) Date of Patent: Aug. 6, 2024

(54) ONLINE MACHINE LEARNING WITH IMMEDIATE REWARDS WHEN REAL REWARDS ARE DELAYED

(71) Applicant: International Business Machines Corporation, Armonk, NY (US)

(72) Inventors: Oznur Alkan, Clonsilla (IE); Djallel Bouneffouf, Wappinger Falls, NY (US); Bei Chen, Blanchardstown (IE); Elizabeth Daly, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 934 days.

(21) Appl. No.: 17/098,829

(22) Filed: Nov. 16, 2020

(65) Prior Publication Data
US 2022/0156637 A1 May 19, 2022

(51) Int. Cl.
*G06G 7/48* (2006.01)
*G06F 16/951* (2019.01)
(Continued)

(52) U.S. Cl.
CPC .......... *G06N 20/00* (2019.01); *G06F 16/951* (2019.01); *G06F 18/214* (2023.01); *G06F 18/2178* (2023.01); *G16H 50/20* (2018.01)

(58) Field of Classification Search
CPC ............ G06N 20/00; G06N 7/01; G06N 3/08; G06N 3/006; G06F 16/951; G06F 18/214; G06F 18/2178; G16H 50/20
See application file for complete search history.

(56) References Cited

U.S. PATENT DOCUMENTS

| 9,754,221 B1 | 9/2017 | Nagaraja |
| 10,558,925 B1 * | 2/2020 | Flor ................ G06N 5/047 |

(Continued)

FOREIGN PATENT DOCUMENTS

| CN | 108027373 A * | 5/2018 | ............ G01N 21/31 |
| CN | 109875522 A * | 6/2019 | ............... A61B 5/00 |

(Continued)

OTHER PUBLICATIONS

Varano, C., "Learning with Delayed Rewards", http:/web.stanford.edu/class/archive/cs/cs221/cs221.1192/2018/restricted/posters/cvarano/poster.pdf, Accessed on Nov. 13, 2020, 1 page.
(Continued)

*Primary Examiner* — Hassan Mrabi
(74) *Attorney, Agent, or Firm* — Scully, Scott, Murphy & Presser, P.C.; Yuanmin Cai

(57) ABSTRACT

An online machine learning model such as an autonomous agent predicts an action. A processor associated with, or running, the online machine learning model observes an environment for an interval of time for a real reward associated with the action. Responsive to determining that the real reward is not received within the interval of time, the processor determines based on a criterion whether to allocate an immediate reward received within the interval of time to the online machine learning model, where the immediate reward is an approximation of the real reward. Responsive to determining that the immediate reward is to be allocated, the processor allocates the immediate reward to the online machine learning model. The online machine learning model further learns or retrains itself based on the immediate reward.

24 Claims, 8 Drawing Sheets

(51) Int. Cl.
  *G06F 18/21* (2023.01)
  *G06F 18/214* (2023.01)
  *G06N 20/00* (2019.01)
  *G16H 50/20* (2018.01)

(56) References Cited

U.S. PATENT DOCUMENTS

| | | | |
|---|---|---|---|
| 10,632,618 B2 | 4/2020 | Pascanu et al. | |
| 10,673,708 B2 | 6/2020 | Parthasarathy et al. | |
| 11,494,836 B2 * | 11/2022 | Cella | H04L 9/50 |
| 11,550,299 B2 * | 1/2023 | Cella | G06Q 30/0206 |
| 11,567,478 B2 * | 1/2023 | Cella | G06V 10/82 |
| 11,586,177 B2 * | 2/2023 | Cella | G06F 9/466 |
| 11,586,178 B2 * | 2/2023 | Cella | G06N 20/20 |
| 2013/0185039 A1 * | 7/2013 | Tesauro | G06Q 10/063 703/6 |
| 2018/0012137 A1 | 1/2018 | Wright et al. | |
| 2018/0225570 A1 | 8/2018 | Eliasmith et al. | |
| 2019/0019082 A1 * | 1/2019 | Dasgupta | G06N 3/063 |
| 2019/0108456 A1 | 4/2019 | Adjaoute | |
| 2020/0175364 A1 | 6/2020 | Xu et al. | |
| 2021/0182351 A1 * | 6/2021 | Shen | G06N 20/00 |
| 2022/0092973 A1 * | 3/2022 | Mohamad Alizadeh Shabestary | G08G 1/08 |
| 2022/0366494 A1 * | 11/2022 | Cella | H04L 9/50 |

FOREIGN PATENT DOCUMENTS

| | | | | |
|---|---|---|---|---|
| WO | 2018/164717 A1 | 9/2019 | | |
| WO | WO-2021015665 A1 * | 1/2021 | | G06Q 30/0235 |
| WO | WO-2021029802 A1 * | 2/2021 | | G05B 13/0265 |

OTHER PUBLICATIONS

Nist, "Nist Cloud Computing Program", http://csrc.nist.gov/groups/SNS/cloud-computing/index.html, Created Dec. 1, 2016, Updated Oct. 6, 2017, 9 pages.

Joulani, P., et al., "Online Learning under Delayed Feedback", Proceedings of the 30th International Conference on Machine Learning, arXiv: 1306.0686v2, Jun. 5, 2013, 14 pages.

Chapelle, O., "Modeling Delayed Feedback in Display Advertising", KDD'14, Aug. 24-27, 2014, 9 pages.

Ktena, S.I., et al., "Addressing Delayed Feedback for Continuous Training with Neural Networks in CTR prediction", arXiv:1907.06558v1, Jul. 15, 2019, 9 pages.

Pike-Burke, C., et al., "Bandits with Delayed, Aggregated Anonymous Feedback", Proceedings of the 35th International Conference on Machines Learning, PLMR, Jul. 2018, 9 pages, vol. 80.

Vernade, C., et al., "Stochastic Bandit Models for Delayed Conversions",arXiv:1706.09186v3, Jul. 12, 2017, 16 pages.

Vernade, C., et al., "Contextual Bandits under Delayed Feedback", arXiv:1807.02089v1, Jul. 5, 2018, 13 pages.

Zhao, X., et al. "Recommendations with Negative Feedback via Pairwise Deep Reinforcement Learning", KDD '18, Aug. 19-23, 2018, arXiv:1802.06501v3, Aug. 10, 2018, 9 pages.

Grover, A., et al., "Best arm identification in multi-armed bandits with delayed feedback", Proceedings of the 21st International Conference on Artificial Intelligence and Statistics (AISTATS) 2018, PMLR, vol. 84, arXiv:1803.10937v1, Mar. 29, 2018, 13 pages.

Hoi, S.C.H., et al., "Online Learning: A Comprehensive Survey", SMU Technical Report 1 (2018) 1-100, Submitted and Published Oct. 2018, arXiv:1802.02871v2, Oct. 22, 2018, 100 pages.

* cited by examiner

ONLINE MACHINE LEARNING WITH IMMEDIATE REWARDS WHEN REAL REWARDS ARE DELAYED

BACKGROUND

The present application relates generally to computers and computer applications, and more particularly to machine learning, online machine learning and training of machine learning models.

Machine learning allows a machine such as a computer processor to automatically learn to perform a task and to improve itself in performing the task from experience without being explicitly programmed. In machine learning such as in reinforcement learning, an autonomous agent such as a computer processor or machine (e.g., referred to also as a learner) learns to perform an action or task based on real feedback or reward obtained from an environment after performing that task. The learning process, for instance, can involve a loop or continuous loop, where the agent performs an action, receives a reward for its action (or penalty from its action) and learns from the received reward (or penalty), the agent performing a future action based on having learned from the received reward or penalty.

In some real practical environments, a reward to an action can be delayed, for example, not received within a time for predicting a subsequent action or subsequent actions. For example, a machine learning model may not receive a reward in an interval of time of an action. Delays in receiving a reward may cause delays in relearning or retraining of the machine learning model, for example, as there is no new feedback information, which the machine learning can use to retrain itself or to continue to learn. For instance, the model is not able to update itself with current or up-to-date information. Such delays can result in the machine learning model predicting or performing one or more subsequent actions not as accurately as it could, for example, if the machine learning model were to have used that reward to predict its subsequent action. For example, delays in rewards can result in the machine learning model taking too long of a time in learning to generate accurate predictions.

BRIEF SUMMARY

The summary of the disclosure is given to aid understanding of a computer system and a method of improving one or more machine learning techniques in generating one or more machine learning models with improved accuracy, for example, in online learning where a reward or rewards, for example, which may be used as feedback information for online real-time training, can be delayed. It should be understood that various aspects and features of the disclosure may advantageously be used separately in some instances, or in combination with other aspects and features of the disclosure in other instances. Accordingly, variations and modifications may be made to the system and/or its method of operation to achieve different effects.

A computer-implemented method, in one aspect, can include an online machine learning model predicting an action. The method can also include observing an environment for an interval of time for a real reward associated with the action. The method can also include, responsive to determining that the real reward is not received within the interval of time, determining based on a criterion whether to allocate an immediate reward received within the interval of time to the online machine learning model, the immediate reward being an approximation of the real reward. The method can also include, responsive to determining that the immediate reward is to be allocated, allocating the immediate reward to the online machine learning model. The online machine learning model can be further trained based on the immediate reward. Advantageously, the method may allow for faster and more accurate online machine learning, for example, in a controlled manner.

A computer-implemented method, in another aspect, can include an online machine learning model predicting an action. The method can also include observing an environment for an interval of time for a real reward associated with the action. The method can also include, responsive to determining that the real reward is not received within the interval of time, determining based on a criterion whether to allocate an immediate reward received within the interval of time to the online machine learning model, the immediate reward being an approximation of the real reward. The method can also include, responsive to determining that the immediate reward is to be allocated, allocating the immediate reward to the online machine learning model. The online machine learning model can be further trained based on the immediate reward. The criterion can include the immediate reward meeting a dynamically defined threshold. Advantageously, the method may allow for faster and more accurate online machine learning, for example, in a dynamically controlled manner.

A computer-implemented method, in yet another aspect, can include an online machine learning model predicting an action. The method can also include observing an environment for an interval of time for a real reward associated with the action. The method can also include, responsive to determining that the real reward is not received within the interval of time, determining based on a criterion whether to allocate an immediate reward received within the interval of time to the online machine learning model, the immediate reward being an approximation of the real reward. The method can also include, responsive to determining that the immediate reward is to be allocated, allocating the immediate reward to the online machine learning model. The online machine learning model can be further trained based on the immediate reward. The criterion can include the immediate reward being lower than an upper bound of an expected reward and higher than a lower bound of the expected reward, the expected reward determined dynamically based on currently maximized reward. Advantageously, the method may allow for faster and more accurate online machine learning, for example, in a dynamically controlled manner.

A computer-implemented method, in another aspect, can include an online machine learning model predicting an action. The method can also include observing an environment for an interval of time for a real reward associated with the action. The method can also include, responsive to determining that the real reward is not received within the interval of time, determining based on a criterion whether to allocate an immediate reward received within the interval of time to the online machine learning model, the immediate reward being an approximation of the real reward. The method can also include, responsive to determining that the immediate reward is to be allocated, allocating the immediate reward to the online machine learning model. The online machine learning model can be further trained based on the immediate reward. In an aspect, the machine learning model can represent an autonomous agent trained to predict content to place on a web site page, the environment can include browsing of the web site page, the real reward can include a purchase event of an item represented in the content and the immediate reward can include a click event of the item. Advantageously, an autonomous agent can be trained faster and more accurately to be able to predict appropriate content to place on a web site page.

A computer-implemented method, in still another aspect, can include an online machine learning model predicting an action. The method can also include observing an environment for an interval of time for a real reward associated with the action. The method can also include, responsive to determining that the real reward is not received within the interval of time, determining based on a criterion whether to allocate an immediate reward received within the interval of time to the online machine learning model, the immediate reward being an approximation of the real reward. The method can also include, responsive to determining that the immediate reward is to be allocated, allocating the immediate reward to the online machine learning model. The online machine learning model can be further trained based on the immediate reward. In an aspect, the machine learning model can represent an autonomous agent trained to predict a medical treatment for curing a disease, the environment can include clinical trials, the real reward can include whether the disease is cured and the immediate reward can include intermediate medical conditions of a patient administered with the medical treatment. Advantageously, an autonomous agent can be trained faster and/or more accurately to be able to predict a treatment for a given disease.

Still in another aspect, a computer-implemented method can include an online machine learning model retraining itself using an immediate reward associated with the action received within a configured time of taking the action, responsive to a delay in receiving an actual reward within the configured time, the immediate reward used in a controlled manner. Advantageously, the method may allow for faster and/or more accurate online machine learning, for example, in a controlled manner.

Various systems can be provided, which can include one or more processors configured to implement one or more of the above-described methods in one or more embodiments.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

Figure 1:
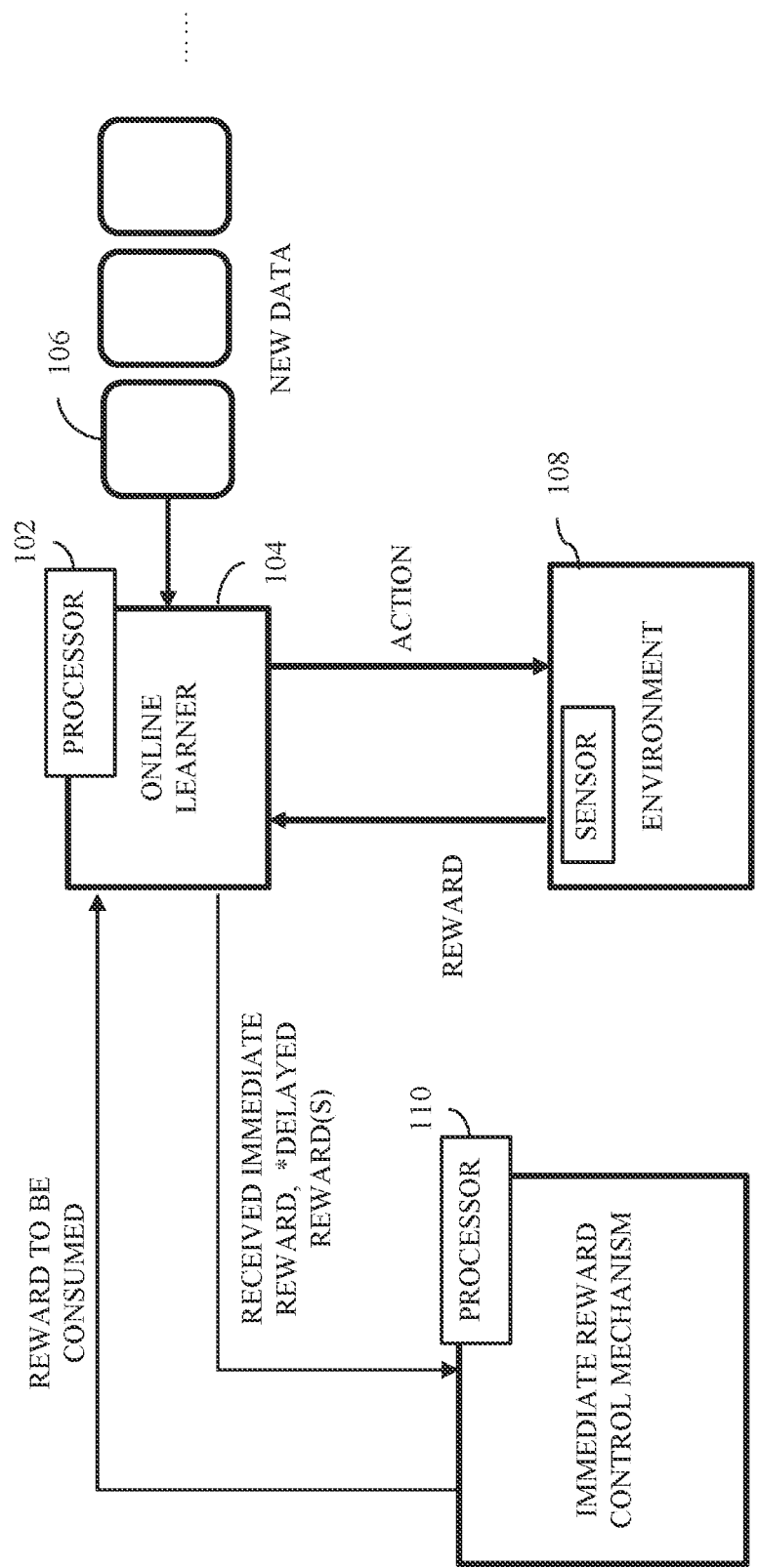
FIG. 1 is a block diagram illustrating components of a system in one embodiment.

Systems and methods can be provided for online learning or online machine learning, for example, where an automatic or autonomous agent such as a computer processor or machine makes a sequence of predictions possibly based on side information, for instance, when real or actual reward is delayed. For example, for each prediction and/or action performed, the autonomous agent may receive an immediate reward and/or an actual delayed reward, where the immediate reward is an approximation of the delayed reward, for example, for use as a feedback in retraining itself in real-time.

Online learning represents a family of machine learning methods, where an autonomous computer-implemented agent (also referred to herein as a learner) attempts to tackle some predictive task by learning from a sequence of data instances one by one at each time. A goal is to maximize the accuracy and/or correctness for the sequence of predictions and/or decisions made by the learner given the knowledge of correct answers to previous predictions. Delayed reward can be an actual true reward that is not obtained instantaneously but received after some delay. For instance, a delayed reward is an actual true reward that is not received within a defined time period or within an interval between actions in a sequence of actions the learner is predicting. Immediate or intermediate reward can be an approximation of the delayed reward which is reviewed immediately or within a defined interval of time after an action is taken by the learner. For example, an immediate reward can be one that is received within a defined time period of taking an action, and for instance, can be information associated with the real reward corresponding to the taken action and received within such defined time period. Another example of an immediate reward can be one that is received after an action is performed, for example, within the interval between actions, for example, received after taking an action and before a next action or a number of next actions is taken.

In an aspect, a system and/or method disclosed herein can provide a technical advantage of allowing an autonomous computer-implement agent to learn to generate more accurate predictions and/or to generate accurate predictions more quickly, for example, so as not to become stale. In another aspect, a system and/method can provide a technical advantage of deciding in a controlled manner when to retrain the computer-implemented agent and/or with what information to retrain the computer-implemented agent.

In one or more embodiment, the systems and methods can be implemented on one or more processors such as computer processors and hardware processors. One or more hardware processors, for example, may include components such as programmable logic devices, microcontrollers, memory devices, and/or other hardware components, which may be configured to perform respective tasks described in the present disclosure. Coupled memory devices may be configured to selectively store instructions executable by one or more hardware processors.

A processor may be a central processing unit (CPU), a graphics processing unit (GPU), a field programmable gate array (FPGA), an application specific integrated circuit (ASIC), another suitable processing component or device, or one or more combinations thereof. The processor may be coupled with a memory device. The memory device may include random access memory (RAM), read-only memory (ROM) or another memory device, and may store data and/or processor instructions for implementing various functionalities associated with the methods and/or systems described herein. The processor may execute computer instructions stored in the memory or received from another computer device or medium.

A system and/or method in one or more embodiments apply or use the immediate or intermediate rewards in instances where the actual rewards are delayed for online learning, for example, to help with the underlying recommendation system. In some aspects, some immediate rewards received can be noisy. In an embodiment, the system and/or method use an immediate reward in a controlled way to minimize its possible unhelpful effect on the performance of the learner and benefit from it in the learning process.

The present disclosure in one or more aspects describe a solution or a setting where in addition to real rewards which are delayed, there are immediate rewards, possibly noisy, received by a leaner. An action can be associated with a delayed reward, for example, not received immediately (e.g., not received within a time period and/or not received within an interval of actions, e.g., where a sequence of actions are predicted or performed), but received after some delay (e.g., after next one or more actions have been performed).

Real-life applications of online learning can have access to both immediate and delayed rewards. Immediate rewards can be considered as side information in the form of partial feedback that can help decision making. For example, consider an electronic commerce (e-commerce) recommendation engine that uses online learning in order to generate item recommendations based on users' previous buying information. In this example, the user clicking the item to view item details is an immediate feedback which gives an idea around user's interest for the item, whereas buying that item later on is the actual however delayed reward for the learner. If the learner consumes only the delayed rewards, it may take too long for the learner to start generating accurate recommendations. In an embodiment, a system and/or method allocates an immediate reward and learns from it, for example, when the real reward is delayed, for example, so that the learner can generate more accurate predictions.

In an embodiment, the system and/or method may allocate the immediate reward in a controlled manner. For example, if the immediate rewards are well aligned with delayed rewards, consuming them can help the learner to reduce the uncertainty towards items and help the recommendation engine to generate accurate recommendations sooner. Immediate or intermediate rewards are an approximation of delayed rewards, and they can sometimes be noisy, for example, not helpful in learning accurately. In an embodiment, the system and/or method consumes immediate rewards in delayed environments in a controlled manner, for example, decides whether to use immediate rewards in online learning based on a criterion. In an embodiment, the system and/or method consumes immediate rewards in delayed environments in a controlled manner through defining an upper and lower bound so that the effect of possible noise in immediate rewards on the online learner's performance is controlled. While the term "reward" is used herein, reward can be a positive or negative (e.g., a penalty) feedback from the environment.

In one or more embodiments, the system and/or method use immediate rewards in addition to the delayed rewards in online learning. The system and/or method in an embodiment implements a strategy to use immediate rewards in a controlled manner so that when the immediate rewards are noisy (e.g., not a good approximation of the corresponding delayed reward), their effect on the learner's performance is controlled. In another embodiment, the system and/or method includes implementing a dynamic upper and lower bound for the immediate rewards.

The following illustrates an example use case. When a seller decides to pass an opportunity to a business associate, the seller uses an associated model to receive business associate recommendations. The seller accepting a recommended associate gives a positive signal to the recommendation engine. The recommendation is regarded as succeeded if the opportunity handled by that recommended business associate ends in a win. However, there exists generally a long time delay between seller accepting a recommended associate and the closed time of the opportunity. In this example, the seller's acceptance is an immediate reward for the recommender which is regarded as an approximation of the delayed reward. The opportunity's end status, which is a win or loss, is the delayed reward for the recommender. In an embodiment, using immediate reward in addition to delayed reward in a controlled manner prevents the online learner from becoming stale, can result in a lower regret and an increase in the accuracy of the generated recommendations.

Another example use case is described as follows. This example use case pertains to clinical trials in medical fields. In medical applications, it is typically unreasonable to assume that the impact of a chosen treatment, out of a set of possible treatments for a patient, will be immediately observable. Patients may provide immediate results of their treatment, which can be used as immediate reward by the learner. The final or delayed reward is "whether the patient is cured". A learner retraining or updating its learning based on such immediate rewards, for example, in a controlled manner, may be able to better predict correct types of treatments for different types of medical conditions.

Yet another example use case can be related to a pay per purchase scenario. Advertisers pay the publisher, for example, a web site owner where the advertisement is placed, only if an item is clicked, and then bought. Using only the buying information may result in a stale learner, which has to wait for delayed feedback (buying information) to be observed. Click information in this scenario provides a positive signal (immediate reward) to the learner about the later buying information. Using this positive signal in a controlled manner can help the learner to learn consumers' or buyers' intentions in a shorter time interval. The learner is able to more accurately predict an action that results in a win. For example, such learning may result in the learner presenting or predicting content such as advertisements that better fit the consumers' interests. Practical use cases and applications can further be found in multiple industries including, but not limited to, manufacturing, medical and healthcare, and sales.

FIG. 1 is a block diagram illustrating components of a system in one embodiment. The components shown include computer-implemented components, for instance, implemented and/or run on one or more hardware processors, or coupled with one or more hardware processors. A processor 102 such as a hardware processor may be running an online machine learning model 104, also referred to as an online learner or learner. The online machine learning model 104 predicts an action or task at each time or time step by learning from a sequence of data instances 106. For example, at a time step, new data 106 can be received, based on which the online machine learning model may perform a predictive task. Data can be received through a series of time steps.

The action can be performed on an environment 108, for example, real physical environment. For example, the processor 102 and/or the online machine learning model 104 can signal the environment 108 to perform the predicted action, and/or actuate the predicted action on the environment 108. The environment 108 can include a machine or a computer processor, which can be coupled with sensor for detecting one or more results associated with the action performed on the environment 108. The environment 108 may compute or calculate a reward associated with the action. There can be a delay between the time or time step of the action and the time the environment 108 provides a reward.

The processor 102 may observe the environment 108 for an interval of time, for example, a defined or predefined period of time. The processor 102, for example, observes the environment 108 for an interval of time for a real or actual reward. The processor 102 can receive from the environment 108 (e.g., a sensor or a processor associated with the environment) a signal representing a presence of a reward and/or the reward (e.g., data or value of the reward). If within the interval of time, the processor 102 does not receive a real reward associated with the action, the processor 102 obtains or receives an immediate reward, which is an approximation or estimation of the real award associated with the action. In an embodiment, the processor 102 may receive an immediate reward and estimate or generate an estimation of the real award based on the values of the immediate reward. In another embodiment, another other component can generate such approximation, for instance, the environment 108 may compute and return the approximation. During this time, the processor 102 may also receive or obtain a delayed reward, which is an actual or real award associated with a previous action taken. At a time or time step, one or more delayed rewards can be received which correspond to one or more previous actions taken. In an embodiment, the delayed reward (an actual or real reward) or rewards can be automatically consumed by the online machine learning model for learning. For instance, in an embodiment, all actual or real rewards can be consumed by the online machine learning model automatically.

In another embodiment, the interval of time can be an interval between one or more actions, e.g., a period between one action to the next action predicted by the online machine learning model. Yet in another embodiment, the interval of time can be a period between one action to a defined number of actions predicted by the online machine learning model.

A processor 110, which can be the same processor at 102 or a different processor, analyzes the received immediate reward, and any received delayed reward, and determines based on a criterion whether to allocate the immediate reward received within the interval of time to the online machine learning model 104. For example, the processor 110 computes or provides a control decision (e.g., decision in a controlled manner) as to whether the immediate reward is to be consumed by the online machine learning model for its learning.

In an embodiment, the criterion includes the immediate reward meeting a dynamically defined threshold. For instance, the criterion which the processor 110 uses in making its decision can be computed dynamically, for example, based on rewards received over iterations of actions taken. In an embodiment, the processor 110 may dynamically compute or define upper and lower bounds based on variances or standard deviations associated with a maximized reward maximized over a number of iterations of actions (e.g., all of the considered number of iterations). In an embodiment, the criterion can be that the immediate reward be lower than an upper bound of an expected reward and higher than a lower bound of the expected reward. The expected reward can be determined dynamically based on maximizing the reward over iterations of actions.

Responsive to determining that the immediate reward is to be allocated, the processor 110 allocates the immediate reward to the online machine learning model 104. For example, the processor 104 may signal the online learner 104 to consume the immediate reward in learning. Responsive to receiving such signal or allocation of the immediate reward, the online machine learning model 104 further learns using the immediate reward to make predictions of actions. For example, the online machine learning model 104 can be re-trained based on the immediate reward. In this way, the online machine learning model 104 make its next action prediction based on having learned from the immediate reward.

In an embodiment, if the processor 110 determines that the immediate reward is not to be allocated, the processor 110 may signal the online machine learning model 104 to not consume the immediate reward.

Figure 2:
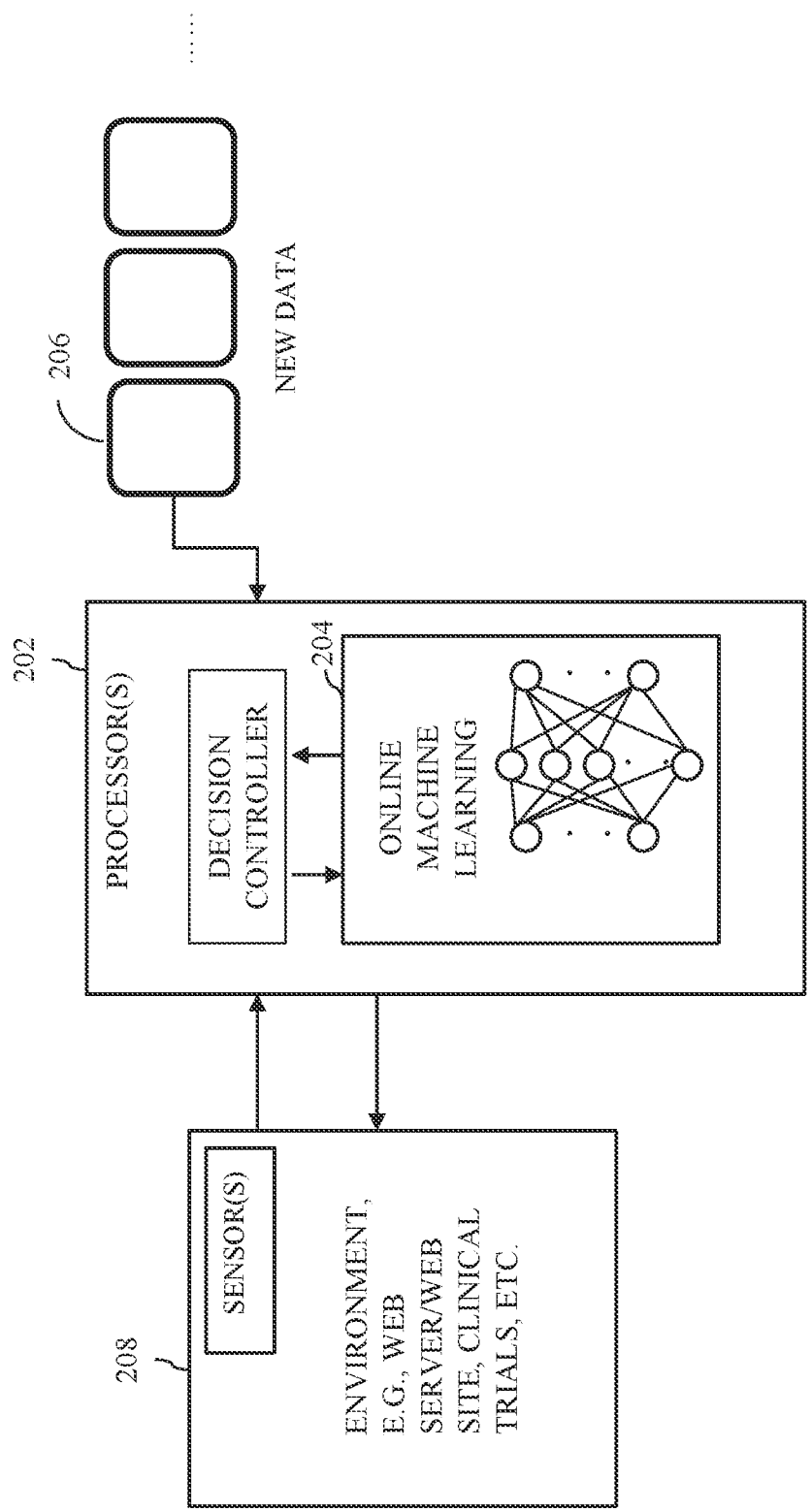
FIG. 2 is another diagram illustrating components of a system in an embodiment.

FIG. 2 is another diagram illustrating components of a system in an embodiment. The components shown include computer-implemented components, for instance, implemented and/or run on one or more hardware processors, or coupled with one or more hardware processors. As described with reference to FIG. 1, an online machine learning model 204 predicts an action, for example, based on a data instance 206 at a given time. Examples of the online machine learning model 204 can include, but not limited to, a reinforcement learning model and a multi-armed bandit. By way of example, the online machine learning model 204 can include a neural network. An A processor 202 may run the online machine learning model 204 and make a controlled decision as to whether to allocate an immediate reward received from an environment 208 to the online machine learning model 204 for use in learning, for example, in an environment where there is a delay is receiving actual or real reward. The processor 202 observes the environment 208 for an interval of time for a real reward associated with the action taken on the environment 208. As described with reference to FIG. 1, the processor 202 determines based on a criterion, which can be dynamic, whether to allocate to the online machine learning model an immediate reward received within the interval of time, the immediate reward being an approximation of the real reward. Responsive to determining that the immediate reward is to be allocated, the processor 202 allocates the immediate reward to the online machine learning model 204 and the online machine learning model 204 further trains itself based on the immediate reward. In one or more embodiment, immediate rewards from the environment can be handled as they are in a dynamic manner, for example, based on maximizing the rewards over all of the number of iterations being considered.

The following describes an immediate award control method or decision control mechanism in an embodiment, for example, performed by the processor 202. In an embodiment, a control method can include deciding whether or not the learner 204 will use the immediate reward in delayed online learning environments. In an embodiment, the control mechanism checks if the immediate reward is within the standard deviation of the expected delayed reward. If the immediate reward is lower than the upper bound of the expected reward and higher than the lower bound of the expected reward the learner 204 can use the immediate reward as it is. Otherwise, the learner 204 does not use the immediate reward. For instance, the immediate reward is considered as being too noisy for use.

In an embodiment, the environment 208 can include a web server providing web pages for browsing of the web site pages. In an embodiment, the online machine learning model 204 can represent an autonomous agent trained to predict content to place on a web site page. The real reward can include a purchase event of an item represented in the content and the immediate reward can include a click event of the item on the web site page.

In another embodiment, the machine learning model 204 can represent an autonomous agent trained to predict a medical treatment for curing a disease. The environment 208 can include clinical trials and/or machines such as one or more computers and sensors involved in such clinical trials. The real reward can include whether the disease is cured and the immediate reward can include intermediate medical conditions of a patient administered with the medical treatment, which can be used to approximate whether the disease would be cured. In one or more other embodiments, the environment 208 can include, but not limited to, manufacturing facilities and/or equipments, other environments such as healthcare, sales, and/or others, for example, where an action is taken and a result of the action can be used in deciding what action to take next.

The following algorithm illustrates a control mechanism. Lines 10-11 show checking whether the immediate reward is within the standard deviation of the expected delayed reward. Line 11 shows that if the immediate reward is lower than the upper bound of the expected reward and higher than the lower bound of the expected reward, the learner will use the immediate reward.

---

Algorithm 1 Immediate Upper Confidence Bound (UCB) Algorithm

1:     Input: α,
2:     for t = $T_0$ + 1 to T do
3:         for all k ∈ K do
4: 
$$\mu_k(t) \leftarrow \frac{\sum_t r_k^i(t) + r_k^j(t)}{n_k^i(t) + n_k^j(t)}$$

5:
$$\sigma_k(t) \leftarrow \alpha \sqrt{\frac{n_k^i(t)}{n_k^j(t)}} \sqrt{\frac{B(t)}{2(n_k^i(t) + n_k^j(t))}}$$

6:
$$\mu_k^j(t) \leftarrow \frac{\sum_t r_k^j(t)}{n_k^j(t)}$$

7:
$$\sigma_k^j(t) \leftarrow \alpha \sqrt{\frac{2\log(t_d)}{n_k^j(t)}}$$

8:         end for
9:         Predict $k_t$ = $argmax_k(\mu_k + \sigma_k)$, and observe environment response $h_t \in \{r_t^i, r_t^j\}$
10:        If $h_t = r_t^i$ then
11:             $r_k(t) = max(\mu_k^j - \sigma_k^j, min(r_k^i(t), \mu_k^j + \sigma_k^j))$
12:        end if
13:     end for

---

$n_k^i(t)$: number of times the arm k received immediate reward.
$n_k^j(t)$: number of times the arm k received delayed reward.
$r_k^i(t)$: the immediate rewards at time t for the arm k.
$r_k^j(t)$: delayed rewards at time t for the arm k.
$\mu_k(t)$: the mean for the arm k at time t, $$\frac{r_k^i(t) + r_k^j(t)}{n_k^i(t) + n_k^j(t)}.$$

$\mu_k^j(t)$: the mean for the arm k at time t for the delayed rewards, $r_k^j(t)/n_k^j(t)$.
$\sigma_k(t)$: the standard deviation for the arm k at time t.
$\sigma_k^j(t)$: the standard deviation for the arm k at time t for the delayed rewards.
$t_d$: total number of times there is delayed rewards (on all arms).
B(t): an increasing function, by definition a function y=f(x) is increasing if the y-value increases as the x-value increases.
$B_e$=(1+e) log(t) increasing function.
α: constant value representing whether to explore or exploit response space, e.g., can be between [0,1].
t: iterations of time, e.g., time step.
$T_0$: start time or time step.
T: end time or time step.
$\mu_k^j$: the mean for the arm k for the delayed rewards.
$\sigma_k^j$: the standard deviation for the arm k for the delayed rewards.
$r_t^i$: immediate reward received at time t.
$r_t^j$: delayed reward received at time t.
$h_t$: environment response received at time t (which can be $r_t^i$ and/or $r_t^j$).

In one or more embodiments, a system and/or method may allocate an immediate reward in the online learning system when the real reward is delayed. For example, the system and/or method may decide whether to use intermediate rewards in an online learning system. The system and/or method may also define a dynamic upper and lower bound for the immediate rewards. The system and/or method may signal the learner to consume the intermediate reward if the intermediate reward is in between the defined upper and lower bounds. The system and/or method may signal the learner not to consume the intermediate reward if the intermediate reward is outside the defined upper and lower bounds.

Figure 3:
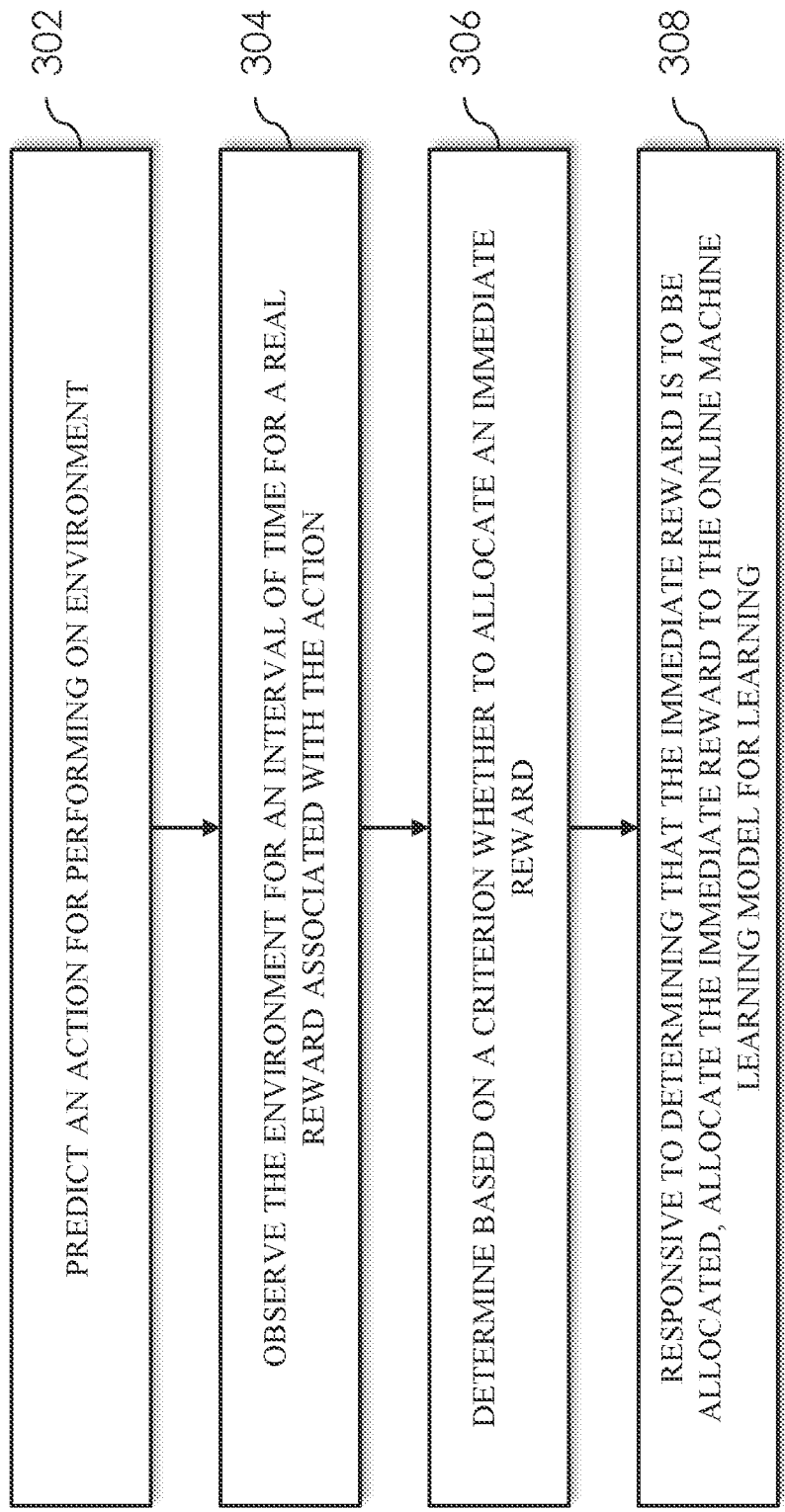
FIG. 3 is a flow diagram illustrating a method in an embodiment.

FIG. 3 is a flow diagram illustrating a method in an embodiment. The method can be implemented, run and/or performed by one or more processors such as hardware processors. At 302, the method can include an online machine learning model such as an autonomous agent predicting an action.

At 304, the method can include observing an environment for an interval of time for a real reward associated with the action. Observing the environment can include receiving from a sensor associated with the environment a signal representing a presence of at least one of the real reward and the immediate award. Observing the environment can include receiving a delayed award and/or an immediate award. In an embodiment, the interval of time can be specified as a defined time period. In another embodiment, the interval of time can be specified as a period between one action to a next action predicted by the online machine learning model. In yet another embodiment, the interval of time can be specified as a period between one action to a defined number of actions predicted by the online machine learning model. For example, the interval of time can be a maximum amount of time (e.g., preconfigured), which the environment is observed for a return of a reward corresponding to an action. By way of example, such maximum amount of time can be configured as a fixed value or a dynamically changing value.

At 306, the method can include, responsive to determining that the real reward is not received within the interval of time, determining based on a criterion whether to allocate an immediate reward received within the interval of time to the online machine learning model. The immediate reward is an approximation of the real reward. For example, in response to performing the predicted action on the environment, the environment may return an immediate reward, e.g., information that could be used to approximate or estimate a reward associated with the predicted action, which may be delayed.

In an embodiment, the criterion used to determine whether the immediate reward should be consumed, can be that the immediate reward meet a dynamically defined threshold. In an embodiment, the dynamically defined threshold can include dynamically defined upper and lower bounds computed based on variances or standard deviations associated with currently maximized reward over iterations, for example, over all iterations. For example, the criterion can include that the immediate reward be lower than an upper bound of an expected reward and higher than a lower bound of an expected reward, where the expected reward is determined dynamically based on currently maximized reward.

At 308, the method can include, responsive to determining that the immediate reward is to be allocated, allocating the immediate reward to the online machine learning model. Using the immediate reward, the online machine learning model retrains itself or learns further based on the immediate reward.

In an embodiment, responsive to determining that the immediate reward is not to be allocated, the method can also include signaling the online machine learning model to not consume the immediate reward for its learning. In an embodiment, the machine learning model can represent an autonomous agent trained to predict content to place on a web site page. The environment can include browsing of the web site page, for example, provided by a web server. The real reward can include a purchase event of an item represented in the content and the immediate reward includes a click event of the item. In another embodiment, the machine learning model can represent an autonomous agent trained to predict a medical treatment for curing a disease. The environment can include one or more machines, processors and or sensors performing clinical trials. The real reward can include whether the disease is cured. The immediate reward can include intermediate medical conditions of a patient administered with the medical treatment, for example, associated with progressing or ameliorating symptoms associated with the disease.

Figure 4:
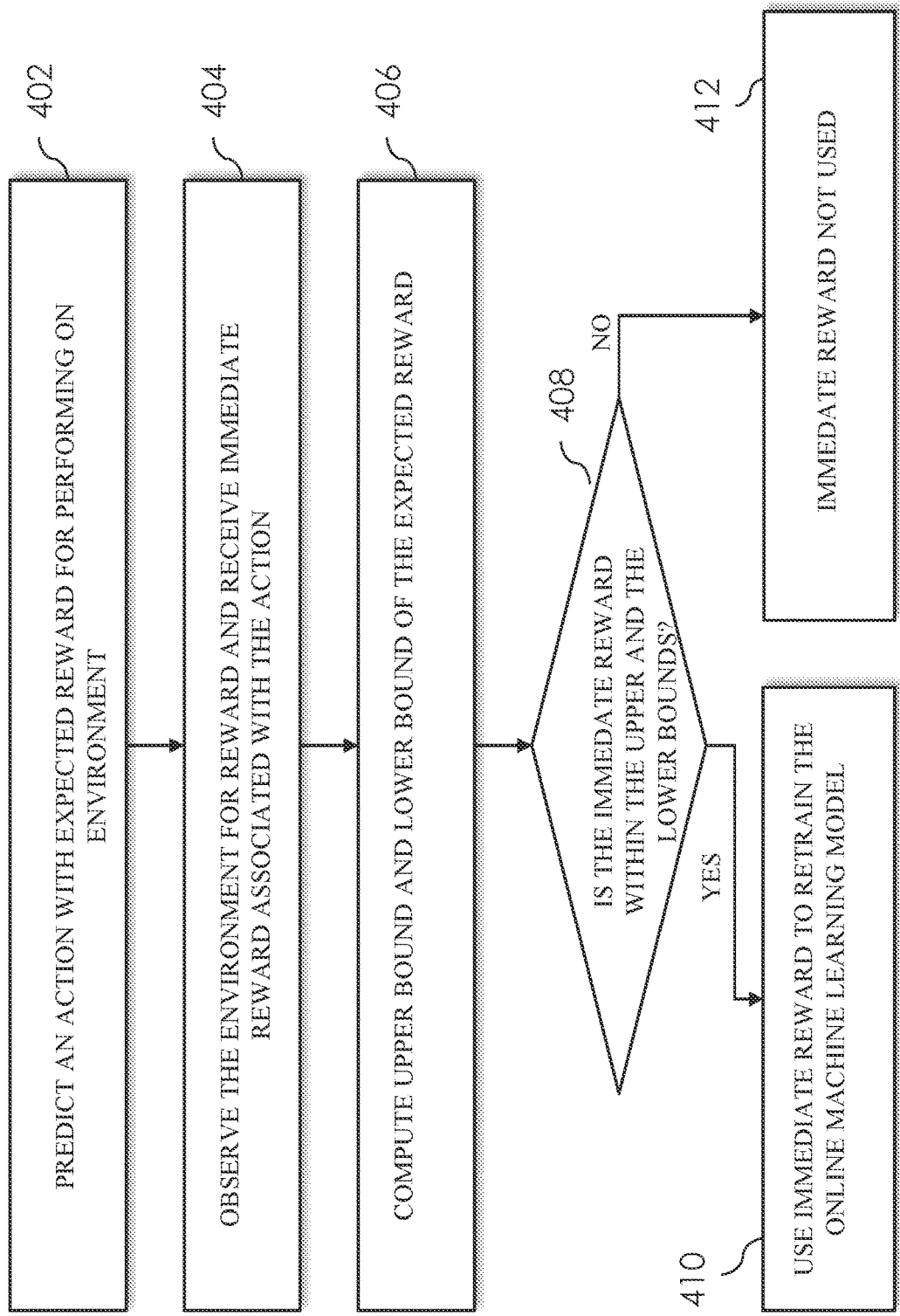
FIG. 4 is a flow diagram illustrating a controlled method of determining immediate rewards to consume in training an online machine learning model in an embodiment.

FIG. 4 is a flow diagram illustrating a controlled method of determining immediate rewards to consume in training an online machine learning model in an embodiment. The method can be implemented, performed, and/or run on one or more processors such as hardware processors. At 402, an online machine learning model predicts an action. For example, the prediction can be made to maximize a return reward, based on learning from past actions and associated rewards. For example, the predicted action has an associated expected reward, which can be an amount that is maximized over all available action choices over all iterations of time steps. The predicted action is applied on an environment. For example, a processor or the online machine learning model may actuate the action or signal the environment to actuate the action.

At 404, the environment is observed for a return reward. For example, at a given time or time step, an immediate reward can be available for the action performed at that time or time step. In another aspect, a delayed reward can also be available, which is associated with an action perform at a previous time or time step. The immediate reward is received. In an aspect, a delayed reward, if available, is received and is automatically consumed by the machine learning model. Based on the immediate reward, an approximation of an actual reward associated with the action performed at the time or time step, is computed. For example, a processor receiving the immediate reward from the environment can approximate an actual reward (e.g., which will be delayed).

At 406, an upper bound and a lower bound of the expected reward are computed. For example, a processor may compute the upper bound and the lower bound of the expected reward. In an embodiment, the upper bound and the lower bound are standard deviations of the expected reward.

At 408, it is determined whether the immediate reward is within the upper and lower bound of the expected reward. At 410, responsive to determining that the immediate reward is within the upper and lower bound of the expected reward, the online machine learning model consumes the immediate for its learning, for example, to retrain itself. At 412, if the immediate reward is outside of the upper and lower bounds, the immediate reward is not used.

Figure 5:
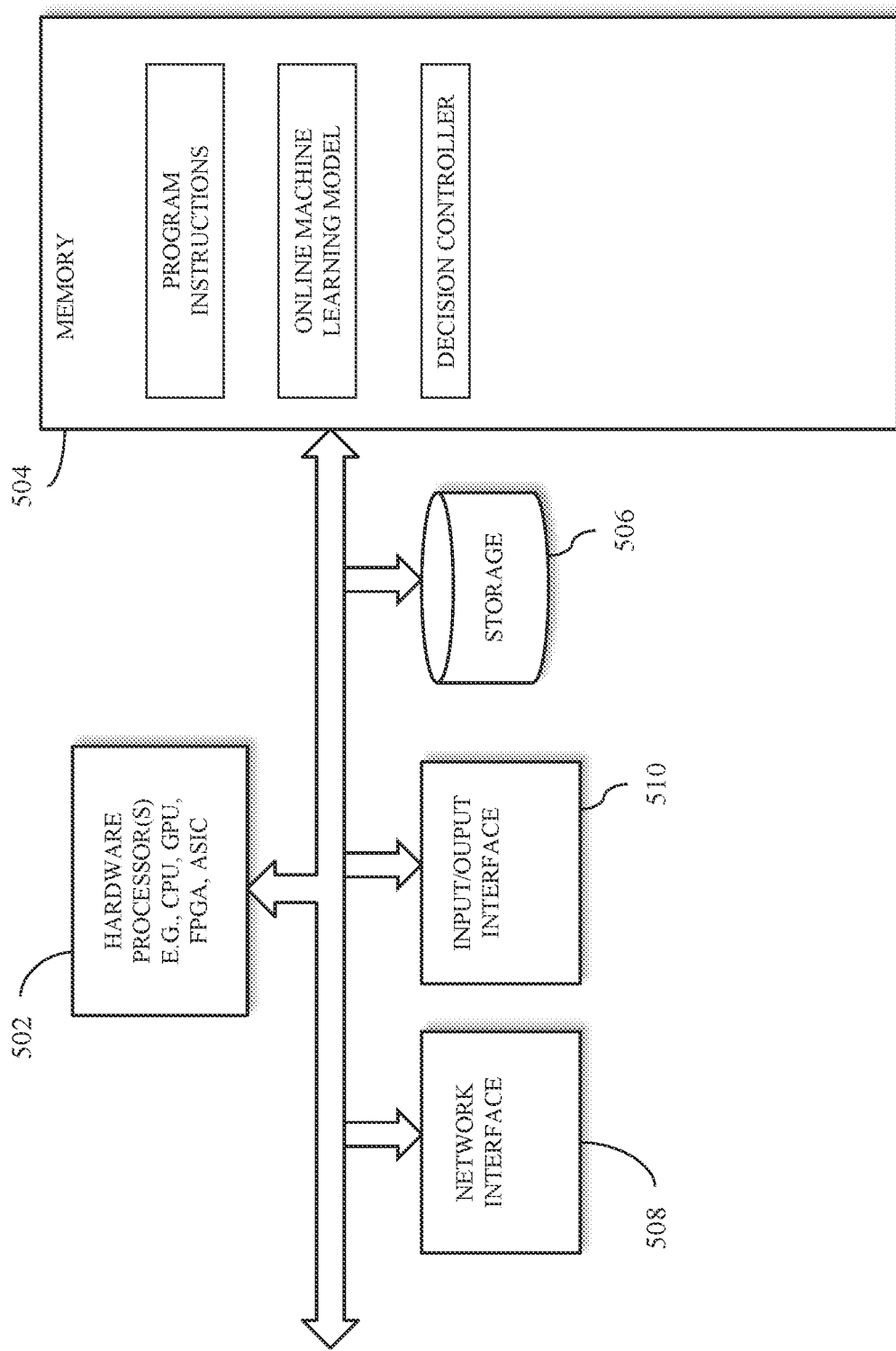
FIG. 5 is a diagram showing components of a system in an embodiment that can perform using immediate reward when there are delayed rewards in online machine learning.

FIG. 5 is a diagram showing components of a system in one embodiment that can perform using immediate reward when there are delayed rewards in online machine learning. One or more hardware processors 502 such as a central processing unit (CPU), a graphic process unit (GPU), and/or a Field Programmable Gate Array (FPGA), an application specific integrated circuit (ASIC), and/or another processor, may be coupled with a memory device 504, and perform online machine learning. A memory device 504 may include random access memory (RAM), read-only memory (ROM) or another memory device, and may store data and/or processor instructions for implementing various functionalities associated with the methods and/or systems described herein. One or more processors 502 may execute computer instructions stored in memory 504 or received from another computer device or medium. A memory device 504 may, for example, store instructions and/or data for functioning of one or more hardware processors 502, and may include an operating system and other program of instructions and/or data. One or more hardware processors 502 may receive input comprising data instances for the online machine learning to perform or predict an action or task. For instance, at least one hardware processor 502 may allow or cause an online machine learning model retraining itself using an immediate reward associated with the action received within a configured time of taking the action, responsive to a delay in receiving an actual reward within the configured time, the immediate reward used in a controlled manner. In one aspect, input data may be stored in a storage device 506 or received via a network interface 508 from a remote device, and may be temporarily loaded into a memory device 504 for the online machine learning to use in its performance. An online machine learning model may be stored on a memory device 504, for example, for running by one or more hardware processors 502. One or more hardware processors 502 may be coupled with interface devices such as a network interface 508 for communicating with remote systems, for example, via a network, and an input/output interface 510 for communicating with input and/or output devices such as a keyboard, mouse, display, and/or others.

Figure 6:
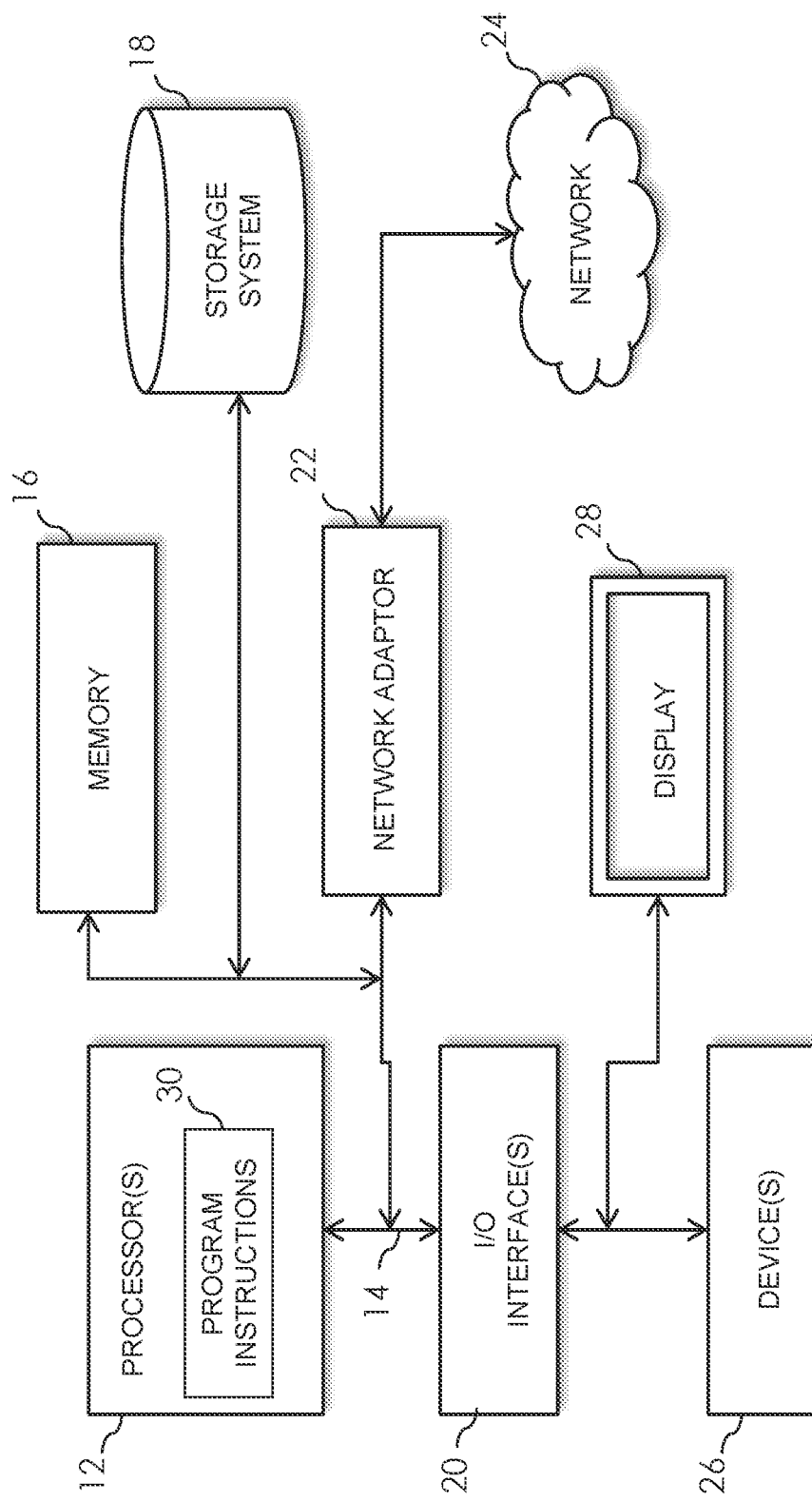
FIG. 6 illustrates a schematic of an example computer or processing system that may implement a system in one embodiment.

FIG. 6 illustrates a schematic of an example computer or processing system that may implement a system in one embodiment. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 6 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being run by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

It is understood in advance that although this disclosure may include a description on cloud computing, implementation of the teachings recited herein are not limited to a cloud computing environment. Rather, embodiments of the present invention are capable of being implemented in conjunction with any other type of computing environment now known or later developed. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 7:
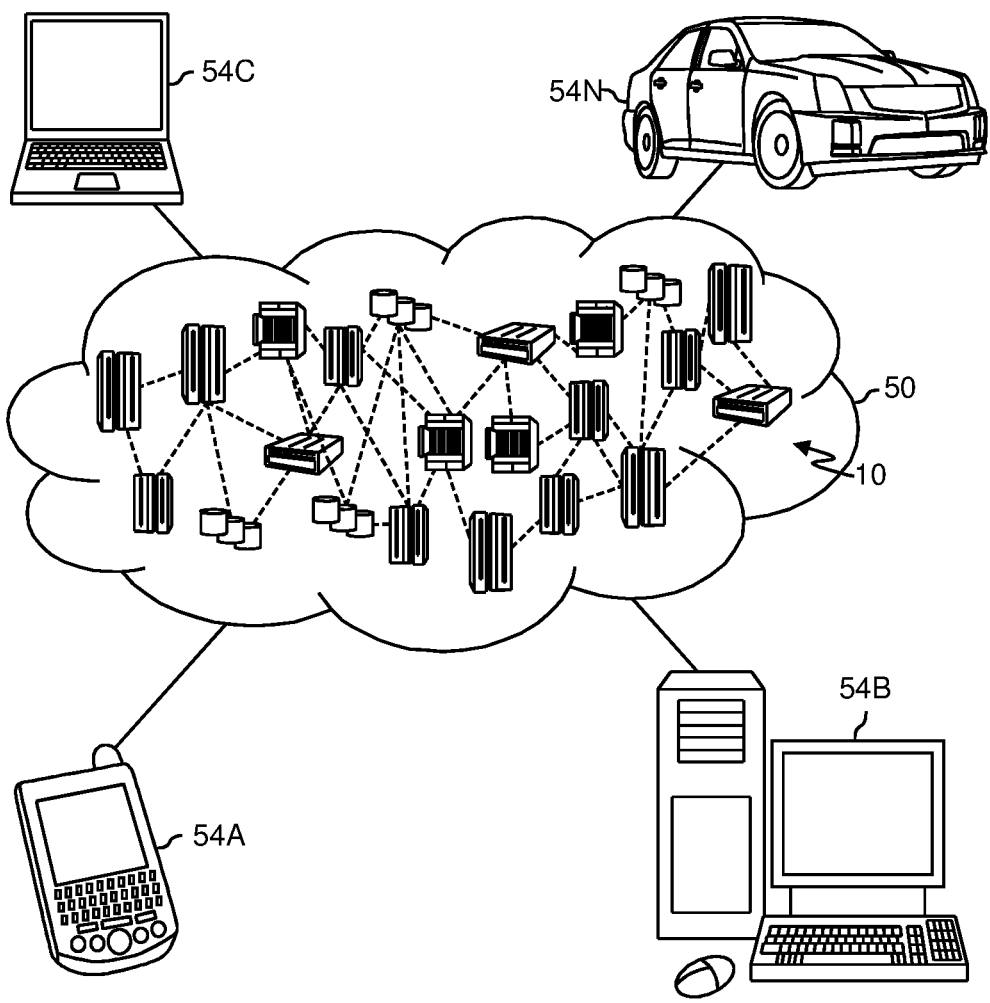
FIG. 7 illustrates a cloud computing environment in one embodiment.

Referring now to FIG. 7, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 10 and cloud computing environment 50 can communicate with any type of computerized device over any type of network and/or network addressable connection (e.g., using a web browser).

Figure 8:
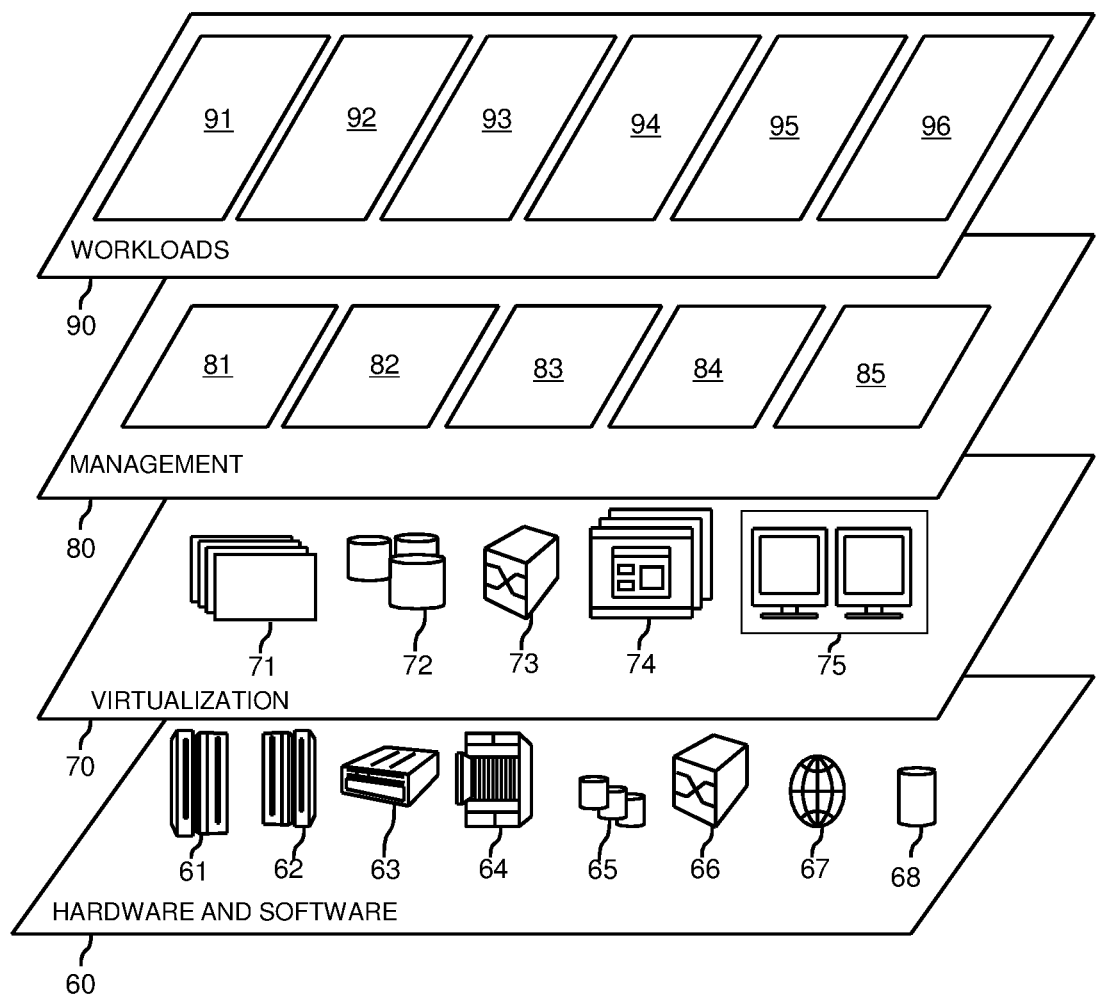
FIG. 8 illustrates a set of functional abstraction layers provided by cloud computing environment in one embodiment of the present disclosure.

Referring now to FIG. 8, a set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and controlling online machine learning in consuming of immediate reward processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, run concurrently, substantially concurrently, in a partially or wholly temporally overlapping manner, or the blocks may sometimes be run in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "or" is an inclusive operator and can mean "and/or", unless the context explicitly or clearly indicates otherwise. It will be further understood that the terms "comprise", "comprises", "comprising", "include", "includes", "including", and/or "having," when used herein, can specify the presence of stated features, integers, steps, operations, elements, and/or components, but do not preclude the presence or addition of one or more other features, integers, steps, operations, elements, components, and/or groups thereof. As used herein, the phrase "in an embodiment" does not necessarily refer to the same embodiment, although it may. As used herein, the phrase "in one embodiment" does not necessarily refer to the same embodiment, although it may. As used herein, the phrase "in another embodiment" does not necessarily refer to a different embodiment, although it may. Further, embodiments and/or components of embodiments can be freely combined with each other unless they are mutually exclusive.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method comprising:
an online machine learning model predicting an action;
observing an environment for an interval of time for a real reward to be received as a result of taking the action that is predicted;
responsive to determining that the real reward is not received within the interval of time, determining based on a criterion whether to allocate an immediate reward received within the interval of time as a result of taking the action that is predicted, to the online machine learning model, the immediate reward being an approximation of the real reward;
responsive to determining that the immediate reward is to be allocated, allocating the immediate reward to the online machine learning model, the online machine learning model being further trained based on the immediate reward, wherein the online machine learning model that is further trained based on the immediate reward, predicts a subsequent action subsequent to the action that is predicted.

2. The method of claim 1, wherein responsive to determining that the immediate reward is not to be allocated, signaling the online machine learning model to not consume the immediate reward.

3. The method of claim 1, wherein the criterion includes the immediate reward meeting a dynamically defined threshold, the dynamically defined threshold controlling an effect on the online machine learning model, of noise in the immediate reward.

4. The method of claim 3, wherein the dynamically defined threshold includes dynamically defined upper and lower bounds based on variances associated with currently maximized reward.

5. The method of claim 1, wherein the criterion includes the immediate reward being lower than an upper bound of an expected reward and higher than a lower bound of the expected reward, the expected reward determined dynamically based on currently maximized reward.

6. The method of claim 1, wherein the observing the environment includes receiving from a sensor associated with the environment a signal representing a presence of at least one of the real reward and the immediate award.

7. The method of claim 1, wherein the interval of time includes a defined time period.

8. The method of claim 1, wherein the interval of time includes a period between one action to a next action predicted by the online machine learning model.

9. The method of claim 1, wherein the interval of time includes a period between one action to a defined number of actions predicted by the online machine learning model.

10. The method of claim 1, wherein the machine learning model represents an autonomous agent trained to predict content to place on a web site page, the environment includes browsing of the web site page, the real reward includes a purchase event of an item represented in the content and the immediate reward includes a click event of the item.

11. The method of claim 1, wherein the machine learning model represents an autonomous agent trained to predict a medical treatment for curing a disease, the environment includes clinical trials, the real reward includes whether the disease is cured and the immediate reward includes intermediate medical conditions of a patient administered with the medical treatment.

12. A system comprising:
a processor; and
a memory device coupled with the processor;
the processor configured to:
predict an action by running an online machine learning model;
observe an environment for an interval of time for a real reward to be received as a result of taking the action that is predicted;
responsive to determining that the real reward is not received within the interval of time, determine based on a criterion whether to allocate an immediate reward received within the interval of time as a result of taking the action that is predicted, to the online machine learning model, the immediate reward being an approximation of the real reward;
responsive to determining that the immediate reward is to be allocated, allocate the immediate reward to the online machine learning model, the online machine learning model being further trained based on the immediate reward, wherein the online machine learning model that is further trained based on the immediate reward, predicts a subsequent action subsequent to the action that is predicted.

13. The system of claim 12, wherein the processor is further configured to, responsive to determining that the immediate reward is not to be allocated, signal the online machine learning model to not consume the immediate reward.

14. The system of claim 12, wherein the criterion includes the immediate reward meeting a dynamically defined threshold, the dynamically defined threshold controlling an effect on the online machine learning model, of noise in the immediate reward.

15. The system of claim 12, wherein the criterion includes the immediate reward being lower than an upper bound of an expected reward and higher than a lower bound of the expected reward, the expected reward determined dynamically based on currently maximized reward.

16. The system of claim 12, wherein the processor is configured to observe the environment includes the processor is configured to receive from a sensor associated with the environment a signal representing a presence of at least one of the real reward and the immediate award.

17. The system of claim 12, wherein the interval of time includes a defined time period.

18. The system of claim 12, wherein the interval of time includes a period between one action to a next action predicted by the online machine learning model.

19. The system of claim 12, wherein the interval of time includes a period between one action to a defined number of actions predicted by the online machine learning model.

20. The system of claim 12, wherein the machine learning model represents an autonomous agent trained to predict content to place on a web site page, the environment includes browsing of the web site page, the real reward includes a purchase event of an item represented in the content and the immediate reward includes a click event of the item.

21. The system of claim 12, wherein the machine learning model represents an autonomous agent trained to predict a medical treatment for curing a disease, the environment includes clinical trials, the real reward includes whether the disease is cured and the immediate reward includes intermediate medical conditions of a patient administered with the medical treatment.

22. A computer program product comprising a computer readable storage medium having program instructions embodied therewith, the program instructions readable by a device to cause the device to:

predict an action by running an online machine learning model;

observe an environment for an interval of time for a real reward to be received as a result of taking the action that is predicted;

responsive to determining that the real reward is not received within the interval of time, determine based on a criterion whether to allocate an immediate reward received within the interval of time as a result of taking the action that is predicted, to the online machine learning model, the immediate reward being an approximation of the real reward;

responsive to determining that the immediate reward is to be allocated, allocate the immediate reward to the online machine learning model, the online machine learning model being further trained based on the immediate reward, wherein the online machine learning model that is further trained based on the immediate reward, predicts a subsequent action subsequent to the action that is predicted.

23. The computer program product of claim 22, wherein the criterion includes the immediate reward meeting a dynamically defined threshold, the dynamically defined threshold controlling an effect on the online machine learning model, of noise in the immediate reward.

24. The computer program product of claim 22, wherein the criterion includes the immediate reward being lower than an upper bound of an expected reward and higher than a lower bound of the expected reward, the expected reward determined dynamically based on currently maximized reward.

* * * * *